US00PP08585P

United States Patent [19]

Stravers

[11] Patent Number: Plant 8,585

[45] Date of Patent: Feb. 8, 1994

[54] GERBERA PLANT: TERBERTOLA

[75] Inventor: Lambertus J. M. Stravers, Kudelstaart, Netherlands

[73] Assignee: Terra Nigra B.V., De Kwakel, Netherlands

[21] Appl. No.: 942,276

[22] Filed: Sep. 9, 1992

[30] Foreign Application Priority Data

May 20, 1988 [NL] Netherlands ..... GRB 855

[51] Int. Cl.[5] ..... A01H 5/00

[52] U.S. Cl. ..... Plt./68.1

[58] Field of Search ..... Plt. 68.1

*Primary Examiner*—James R. Feyrer
*Assistant Examiner*—Elizabeth C. Kemmerer

[57] ABSTRACT

A new and distinct cultivar of Gerbera plant named 'Terbertola', characterized by its single type, a red ray floret which is a solid red color throughout, a red-purple disc floret the outermost florets of which show white stigmas and the middle florets of which show yellow anthers, red perianth lobe color and 100 mm overall flower diameter is disclosed.

1 Drawing Sheet

BACKGROUND OF THE INVENTION

The present invention comprises a new and distinct cultivar of *Gerbera jamesonni*, referred to by the cultivar name 'Terbertola'. 'Terbertola' was originated from a hybridisation program in De Kwakel, The Netherlands in 1984. The female parent was 'Terracorso' -79.78- (registration number 6509 06/09-1984) and was available outside Terra Nigra; and the male parent was unnamed seedling 81.222 which was not available to others outside the company. Both parents had not been registered in the U.S.A. Female parent 'Terracorso'has a pink color, no black center, a smaller center, longer stems, and a higher production than 'Terbertola'. The male parent 81.222 has a purple color, black center, and a lower production than 'Terbertola'. The new cultivar was selected by me from the progeny of the stated parentage on or about November 1984. The first asexual reproduction of 'Terbertola' was accomplished when vegetative cuttings were taken on May 1985 in De Kwakel. The new cultivar is presently being propagated by cuttings and tissue culture. Horticultural examination of selected units initiated November 1986 has demonstrated that the combination of characteristics as herein disclosed for 'Terbetola' are firmly fixed and are retained through successive generations of asexual reproduction. The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terbertola', which in combination distinguish this Gerbera from its parents and all other varieties of which I am aware:

1. Type: Single.
2. Color of ray floret: Distinctive red.
3. Color of disc floret: Red-purple.
4. Color of perianthy lobe: Red.
5. Diameter of flower head: Medium 100 mm.

Of the many commercial cultivars known to me, there is no cultivar similar in comparison to 'Terbertola'.

BRIEF DESCRIPTION OF THE FIGURE OF THE DRAWINGS

The accompanying photographic drawing shows typical inforescence and foliage characteristics nearly true as possible. In the following description, color references are made to The Royal Horticultural Society Color Chart (RHS). The color values were determined at 11:30 a.m. on Mar. 31, 1988 under natural light at De Kwakel.

BOTANICAL DESCRIPTION OF THE PLANT

Botanical: *Gerbera jamessonii* cv. Terbertola.

1. INFLORESCENCE

A. Capitulum:
- *Form.*—Cup shaped.
- *Type.*—Single.
- *Diameter across face.*—100 mm.

B. Corolla of ray florets:
- *Color (general tonality from a distance of 3 meters-).*—Red.
- *Color (topside).*—RHS 45B.
- *Color (bottom).*—RHS 45C.

C. Corolla of disc florets:
- *Color (mature)* —Purple RHS 187B.
- *Color (immature).*—Purple RHS 187B.

D. Reproductive organs:
- *Stigma.*—Yellow RHS 13A.
- *Anthers.*—Dark yellow RHS 15A.
- *Pappus.*—Purple RHS 185A.

2. PLANT

A. General Appearance:.
- *Height.*—40 cm.

B. Foliage:
- *Color (abaxial).*—RHS 147A.
- *Color (adaxial).*—RHS 138B.
- *Shape.*—The angle of apex: right angle. The shape of apex: pointed. The margin of lobes: sinuate.

C. Disease resistance:
No special disease resistance.

3. OTHER CHARACTERISTICS

The following traits have been repeatedly observed and are determined to be basic characteristics of 'Terbertola', which in combination distinguish this Gerbera as a new and distinct cultivar.

Leaf blade:

*Length.*—Medium/long (52 cm).

*Width.*—Medium (23 cm).

*Thickness.*—Medium.

*Blistering.*—Medium/Stark.

*Pubescence.*—On upper side (midrib excluded) of the leaf blade is medium.

*Depth of cuts or incisions in leaf.*—Basal part: Medium. Central part: Deep. Distal part: Medium.

*Color.*—Upperside of the leaf blade is medium green (RHS 147A).

*Glossiness on upper side.*—Medium.

*Angle of apex.*—Weakly obtuse.

*Shape of apex.*—Pointed.

*Margin of lobes.*—Sinuate.

*Extensions of margin.*—Small.

*Petiole length.*—Medium.

*Petiole anthocyanin coloration.*—Present.

Peduncle:

*Length.*—Medium (65 cm).

*Cross section.*—Round.

*Tendency to fasciation.*—Absent.

*Thickness.*—Medium.

*Strength.*—Strong.

*Pubescence.*—Medium.

*Color.*—Medium green.

*Anthocyanin coloration.*—At base: Absent. At top: Absent.

*Involucral bracts.*—Present.

Flower head:

*Type.*—Single.

*Diameter.*—Medium (approx. 100 mm).

*Involucre.*—Height: Medium (14 mm). Diameter: Medium/Large. Number of bracts: Medium (44). Longitudinal axis of bracts of inner rows: Reflexing. Anthocyanin: Absent. Pubescence: Medium.

*Ray florets.*—Number: Medium (47). Shape: Narrow elliptic. Longitudinal axis outer row: Reflexing.

*Outer ray florets.*—Cross section: Flat. Length: Medium (45 mm). Width: Medium. Longitudinal folding: Medium. Angle or apex: Obtuse. Shape of apex: Rounded. Incisions of apex: Absent. Length of free petals: Absent. Edge of different color: Absent. Striation: Absent. Claw spot: Present.

Disc florets:

*Diameter.*—Medium.

*Main color perianth lobes.*—Female flowers: red RHS 43A. Male flowers: red RHS 44A. The innermost disc florets are closed, the next outermost show yellow anthers, and the outermost disc florets show white stigmas.

Reproductive parts:

*Stigma.*—Main color yellow (RHS 13C).

*Anthers.*—Main color dark yellow (RHS 15A). Color of top relative to other parts id darker. Longitudinal striping: Present.

*Pappus.*—Main color purple (RHS 185A). Color of top relative to other parts is darker. Orientation: Level of top relative to closed disc florets is below.

*Fertiliy.*—Very high fertility; good seed production.

I claim:

1. A new and distinct cultivar of Gerbera plant named 'Terbertola', as illustrated and described, characterized by its single type, a red ray floret which is a solid red color throughout, a red-purple disc floret the outermost florets of which show white stigmas and the middle floret of which show yellow anthers, red perianth lobe color and 100 mm overall flower diameter.

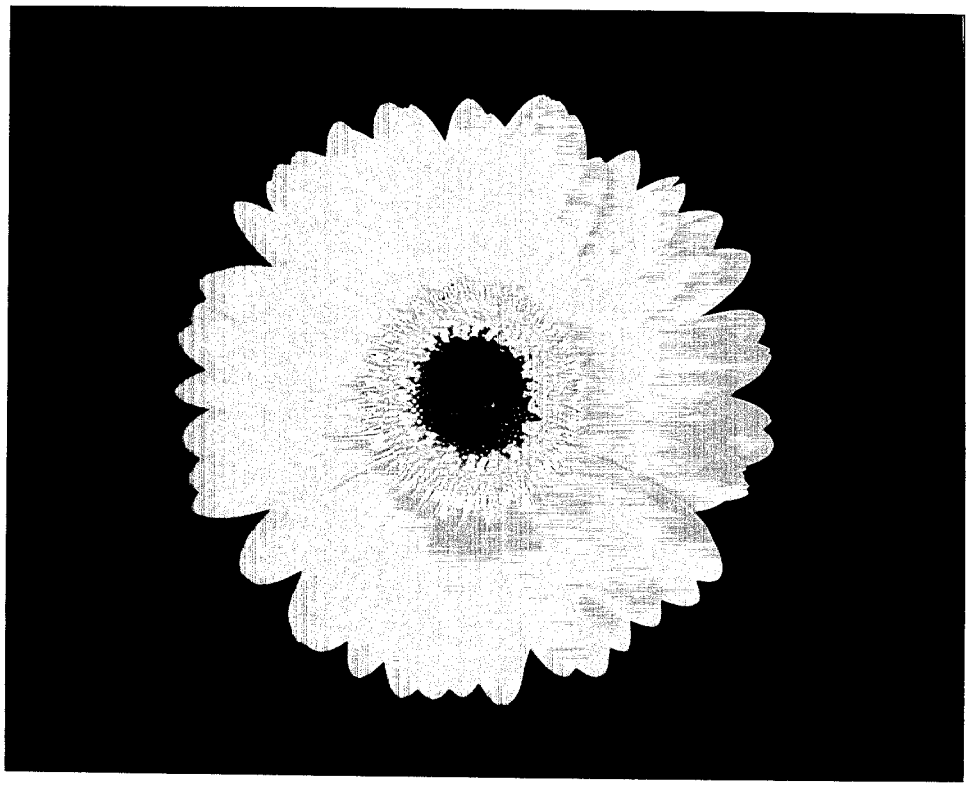

* * * * *